(12) United States Patent
Berndt et al.

(10) Patent No.: US 10,085,890 B2
(45) Date of Patent: Oct. 2, 2018

(54) WOUND DRESSING, GLOVE AND METHOD FOR PRODUCTION OF A WOUND DRESSING

(75) Inventors: Erik Berndt, Aachen (DE); Jürgen Steffes, Puschendorf (DE)

(73) Assignee: PREVOR INTERNATIONAL, Paris (FR)

( * ) Notice: Subject to any disclaimer, the term of this patent is extended or adjusted under 35 U.S.C. 154(b) by 2224 days.

(21) Appl. No.: 10/466,374

(22) PCT Filed: Jan. 7, 2002

(86) PCT No.: PCT/DE02/00008
§ 371 (c)(1),
(2), (4) Date: Nov. 18, 2003

(87) PCT Pub. No.: WO02/053073
PCT Pub. Date: Jul. 11, 2002

(65) Prior Publication Data
US 2005/0159694 A1   Jul. 21, 2005

(30) Foreign Application Priority Data

Jan. 7, 2001 (DE) ................. 101 00 304

(51) Int. Cl.
*A61F 13/00* (2006.01)
*A61F 13/10* (2006.01)
(52) U.S. Cl.
CPC .. *A61F 13/00034* (2013.01); *A61F 13/00025* (2013.01); *A61F 13/00995* (2013.01); *A61F 13/104* (2013.01); *A61F 2013/00131* (2013.01); *A61F 2013/00157* (2013.01); *A61F 2013/00238* (2013.01); *A61F 2013/00255* (2013.01); *A61F 2013/00519* (2013.01); *A61F 2013/00863* (2013.01)

(58) Field of Classification Search
CPC .. A61F 13/00; A61F 13/0004; A61F 13/0008; A61F 13/00012; A61F 13/00021; A61F 13/00025; A61F 13/00034; A61F 13/00038; A61F 13/02; A61F 13/0276; B32B 1/00; B32B 5/00; B32B 5/026
USPC ........... 602/42–43, 47–48, 50, 55–56, 8, 58; 428/98, 107, 113, 172, 190, 221
See application file for complete search history.

(56) References Cited

U.S. PATENT DOCUMENTS

| | | | |
|---|---|---|---|
| 2,823,444 A | | 2/1958 | Davies et al. |
| 3,539,436 A | * | 11/1970 | Hisashi ..................... 428/100 |
| 4,051,848 A | | 10/1977 | Levine |
| 4,671,266 A | * | 6/1987 | Lengyel et al. ............. 602/45 |

(Continued)

FOREIGN PATENT DOCUMENTS

| | | |
|---|---|---|
| DE | 465330 | 5/1937 |
| DE | 742041 | 3/1944 |

(Continued)

*Primary Examiner* — Tarla Patel
(74) *Attorney, Agent, or Firm* — Henry M. Feiereisen; Ursala B. Day

(57) ABSTRACT

According to the invention, a wound dressing may be further developed, whereby a wound dressing made from a planar structure with a first main direction of extension and at least one further main direction of extension, whereby the textile planar structure, at least along the main directions of extension comprises extensibility properties which differ by less than 80%, preferably less than 50%.

17 Claims, 1 Drawing Sheet

(56) References Cited

U.S. PATENT DOCUMENTS

| | | | |
|---|---|---|---|
| 4,725,279 A | | 2/1988 | Woodroof |
| 5,437,621 A | * | 8/1995 | Andrews et al. ............... 602/42 |
| 5,447,505 A | * | 9/1995 | Valentine et al. ............ 604/304 |
| 5,725,487 A | * | 3/1998 | Freeman et al. .................. 602/8 |
| 5,823,978 A | * | 10/1998 | Cueman et al. .................. 602/6 |
| 5,939,339 A | | 8/1999 | Delmore et al. |
| 6,627,785 B1 | * | 9/2003 | Edwards et al. ............... 602/48 |

FOREIGN PATENT DOCUMENTS

| | | |
|---|---|---|
| DE | 27 08 822 | 9/1977 |
| GB | 741659 | 12/1955 |

* cited by examiner

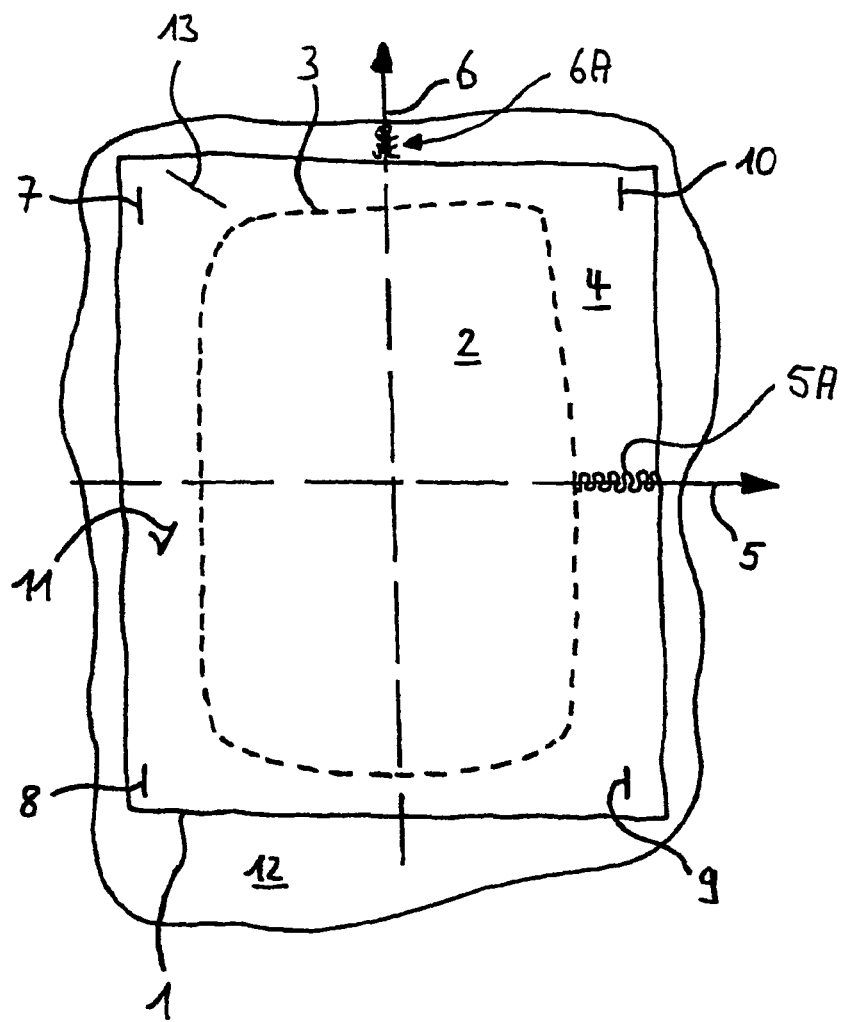

WOUND DRESSING, GLOVE AND METHOD FOR PRODUCTION OF A WOUND DRESSING

BACKGROUND OF THE INVENTION

The invention refers to a wound dressing made from a textile planar structure having a textile surface and having a first main direction of extension and with at least a further main direction of extension, a glove for dressing a wound and a method for producing the wound dressing made from a textile planar structure.

From the prior art, several wound dressing products for dressing wounds are known, in particular also for superficial second degree skin injuries, respectively split skin graft sites.

For example, split skin graft sites are oftentimes treated with gauze saturated with salve (Branolind-gauze, PVP-iodide gauze, chlorhexidine gauze and similar) which are mostly placed onto the wound with a protective bandage. Several days after removal of the protective bandage which covers the salve gauze, an open wound treatment can be started, wherein the gauze in most cases becomes hard and inflexible. This causes considerable pain to the patient, in particular when the patient is to be moved.

It is also disadvantageous that the salve gauze remains on the injured site until after reepithelization spontaneous removal is done, so that a reliable evaluation of the wound healing is made very difficult if not impossible. As compared with other products, when using salve gauzes the reepithelization period is often essentially prolonged. In particular, treatment of thermal and chemical skin damage with salves (e.g. silver sulfadiazine) requires daily change of the bandages, which for the most part is very painful for the patient, as the salve residues have to be removed from the base of the wound by mechanical means.

Hydrocolloid bandages are also known for the treatment of wounds, (e.g. Varihaesive) or foil bandages (e.g. Opsite-foil) which, as compared to the salve bandages are characterized by a distinctly lower pain level experienced by the patient. When utilizing such hydrocolloid bandages, a liquid-/hydrogel blister forms (with use of foil bandages only wound secretion) between the wound base and the wound dressing. On average, these bandages must be changed every 5 days and in the meantime do not permit adequate evaluation of the wound. Also, application on awkward sites, as for example the transitional part from leg to bottom is also extraordinarily difficult and therefore possible only in limited ways, since due to their lack of elasticity, the hydrogel plates separate from the awkward sites and oftentimes a mixture of hydrogel and wound secretion runs out from the area of the hydrocolloid bandages. In addition, the hydrocolloid bandages require a large overlap of area surface with surrounding healthy tissue.

Furthermore, from the U.S. Pat. No. 4,725,279, a polyamid textile structure is known under the name "Biobrane". According thereto, after a cleaning of the wound, a treatment follows through attaching the "Biobrane" in connection with applying a protective bandage. This protective bandage is removed during the duration of the treatment, whereby then an open wound treatment can be carried out. The polyamid structure remains adhering until the complete healing of the wound, after which it peels of spontaneously. Due to the elasticity of the polyamide structure and lack for the need to change bandages, patients rarely suffer from pain when being treated with "Biobrane".

It is also disadvantageous, that upon treating a wound infection, the bordering surface wound-wound dressing cannot be reached or can only be inadequately reached with hydrophilic local topical, since the surface of the wound dressing facing away from the body is mostly coated with silicone.

Also known are wound bandages that are composed of several superposed components. For example, laid open publication DE 27 088 22 describes a wound dressing produced from several layers of knitted material as well as an outer protective layer. While this wound dressing has good elastic properties, the elasticity of the wound dressing with extensions in various directions, differ extensively from each other, so that this type of wound bandage cannot follow the patient's body movement in an adequate manner.

Furthermore, this is a drawback of also other dressings in the afore-described prior art.

Up until now, obviously no wound dressing has been provided with the capacity to stretch in nearly all directions, and essentially exhibiting the capacity for stretching into the main extension directions of a wound dressing, and which would stretch in way to especially correspond to the skin stretching properties of a patient or surpasses them.

SUMMARY OF THE INVENTION

The object of the invention is thus, to further develop generic wound dressings and to provide a wound dressing of a textile planar structure that is extendable into a first main direction of extension and having at least one further main direction of extension, wherein the textile planar structures have a capacity of extension deviating from each other by less than 80%, preferably less than 50%.

The term "textile planar structure" according to the invention is defined as referring to all types of textiles, in particular also stitched goods, for example knit fabrics and/or weaves and all types of knitted and woven material. A weave has the advantage that when cutting the bandage to size, it is less prone to bunch up as compared to other materials. On the other hand, a knitted material is characterized especially by its good elastic properties.

It is understood in this context, that the textile planar structure can also be produced from a variety of fibers such as natural or synthetic fiber and/or can be produced of another variety of fibers or respectively a variety of filaments.

Essentially, all types of possible materials can be utilized so long that they are biocompatible and do not cause inflammation or have only very low inflammatory properties. The preferred production method by which the textile planar structure is produced is by way of chain weaving machines or Raschel warp-knitting machines and byway of knitting machines of the type that produces circular knits or flat knits.

The term "first main direction of extension" is preferably defined as that direction, which extends along a row of stitches in a textile planar structure.

The term "further main direction of extension" is preferably defined as that direction, which extends along a row of stitch wales in a textile planar structure and thus deviates from the term "first main direction of extension". Preferably the "further main direction of extension" extends orthogonal to the first "first main direction of extension", but can also include any other direction relative to the "first main direction of extension".

In connection with the use of a weave for the textile planar structure, the main direction of extension can for example run in the direction of the warp, respectively in the direction of the weft.

It is particularly advantageous, when the textile planar structure exhibits essentially the same extensibility properties in the two main directions of extension.

The wound dressings have longitudinal extension and a transverse extension and describes in an especially simple manner the structure of the wound dressing, wherein even with this simple embodiment of the wound dressing structure, to date, no wound dressing has been however realized with essentially the identical stretching property at least in the main direction of extension along a longitudinal axis, and in a main direction of extension along a transverse axis.

In case that elastomeric fibers, optionally elastomeric threads are added in the textile planar structure then stretching properties are realized at least with respect to the main direction of extension, which deviate from each other only by about 20% or less.

Thereby, the wound dressing obtains especially homogenous stretching properties, which makes it especially suited to be adaptable to the various motions of a patient's body and thus can follow its motions.

This type of feature, among others influences the wearing comfort for the patient, as well as the course of healing and the entire course of treatment in a positive manner, whereby an essentially pain free respectively pain-shortening healing process is realized for the patient.

The term "stretching property" in the context of the invention is defined as a "stretching $\varepsilon$" which describes a ratio of a change in length $\Delta L = L1-L0/L0$ within the framework of maximum pull force extension and which for example can be expressed as a per cent value.

In order to evaluate the stretching properties in an adequate manner, a sample is pre-tensioned with a tension of a preliminary force of 0.1 N. Subsequently, the continuous increase in force will be measured, whereby the example will be continuously further stretched. The force is increased to a degree until a maximum value is reached and upon further stretching then drops again. For example, the sample is being stretched by 40 mm before the maximum pull force applies.

In order to adequately describe and compare the "stretching $\varepsilon$", an even force application with respect to the different directions of extension of the textile planar structure is assumed as a precondition.

Those skilled in the art recognize that the introduction of the feature "stretching $\varepsilon$" a value relating to the elasticity of a textile planar structure can also be described.

It is advantageous when the textile planar structure exhibits a "stretching $\varepsilon$" value at least in direction of the main directions of extension of a "stretching $\varepsilon$" of less than 700% preferably of less than 500%. It has been shown that a "stretching $\varepsilon$" in. any event, is sufficient to behave in correspondence to the tissue stretching on a body's surface. Any further increase in stretching $\varepsilon$ carries no further advantage but instead increases the complexity and cost of production of the textile planar structure.

It is particularly advantageous, to provide the textile planar structure at least in the main direction of extension with a stretching $\varepsilon$ of greater than 30%, preferably greater than 50%. Particularly so, when the body surface to be treated with the textile planar structure exhibits a tissue stretching $\varepsilon$ of about 50% it is. particularly efficient when the stretching $\varepsilon$ of the textile planar structure exceeds the stretching $\varepsilon$ of the body respectively approaches this value.

In an advantageous variant of an embodiment the stretching $\varepsilon$ has a value in the range between 60% and 400%, preferably a value of between 100% and 300%. It has been shown that a stretching $\varepsilon$ in the range of from 100% to 300% is particularly suitable for a wound dressing. A wound dressing with such a stretching $\varepsilon$ adapts particularly to a wound to be covered and thus adjusts to almost all motions of the patient without any problems. Thereby, the pain level for the patient is substantially reduced and healing of the wound can proceed more rapidly and with fewer problems as compared to comparable wound dressings of the prior art.

Adjusting the elastic properties of the wound dressing can for example be obtained through a suitable binding of the textile planar structure and/or through post treatment with heat of the textile planar structure. For example, post treatment may be carried out by means of a tension frame, whereby desired properties are fixed in the textile planar structure under impact of temperature changes. For this purpose, the textile planar structure can be inserted into an oven either in the form as a pre-stressed material or as lose material and to remain there until the desired properties have been fixed within the material.

The wound dressing is also simple from a constructional point of view, particularly when the textile planar structure is constructed in a single layer. Another advantage of a single layered textile planar structure is the ability of conforming well to the body contours.

In order to realize the highest possible flexibility, respectively the elasticity of the wound dressing, it is advantageous, when the wound dressing is configured with a thickness of less than 6 mm, preferably a thickness of less than 2 mm.

In order to obtain certain firmness, so that upon removal of the dressing from the wound, the textile planar structure has sufficient firmness and does not easily tear, it is advantageous that the wound dressing has a thickness of more than 0.05 mm and preferably more than 0.1 mm.

The afore-stated thickness dimensions of the textile planar structure allows in particular a relatively wide freedom of movement for the patient, so physical therapy can be also carried out. Thus a contracture prophylaxis is made possible right at the start of treatment.

In a further variant of the embodiment, the wound dressing is provided with pores having a diameter of less than 2 mm, preferably a diameter of less than 0.3 mm.

It is advantageous, that the pores have a diameter of more than 0.02 mm preferably a diameter of more than 0.08 mm.

An advantageous porosity is created by means of these pores, which among other things confers good permeability to the wound dressing, which in turn has beneficial advantages for the treatment of the wound. A good permeability respectively homogenous permeability is particularly the result of the structural properties of the textile planar structure of the wound dressing.

The permeability provides a semi-occlusive wound dressing, whereby gas- and fluid exchange can occur between the wound and the environment of the wound. With respect to the gas exchange, an excellent imitation of the natural function of the skin is therefore achieved.

This means that the moist wound, as compared to the treatment with a perforated wound dressing, can dry in a particular even manner.

It is furthermore advantageous that with the pores an excellent adherence as compared to the area of damage is realized, especially since wound secretion has the tendency to run through the pores where it conglutinates. Thus, the wound dressing receives a particularly good connection to the wound, respectively the injured site.

It is of further advantage that a larger amount of wound secretion is able to drain through the pores.

As afore-stated, a multitude of materials are suited for the production of the textile planar structure, wherein it is however advantageous when the textile planar structure incorporates at least some silk. Silk is particularly suitable for production of the textile planar structure used as a wound dressing, since the afore-stated stretching properties are particularly well realized when silk is used as a component.

In addition, silk has a good capacity for taking up moisture. Silk can also take up for example alkaline and mineral acids under formation of salts.

An especially preferred variant of an embodiment, the textile planar structure contains more than 30% silk, preferably more than 70% silk. With a high percentage of silk, a good wound treatment is realized as the silk exhibits the property of particularly high moisture uptake.

Particularly with respect to the use of silk used in the construction of the textile planar structure, at the occurrence of an infection, any moisture formation and/or blister formation at the wound can be detected from the outside, without the need for removal of the damage area. Checking up is therefore unnecessary during the course of wound healing, so that the healing process can continue in uninterrupted manner.

Furthermore, silk possess good water and gas permeability, so that it is possible to treat the wound externally by means of hydrophilic solutions utilized for wound treatment (e.g. PVP-iodine solution, Lavasept-solution). Such treatment is not possible in particular with dressings of the type having a non-permeable outer coating. In particular, with respect to the wound the diagnosis is facilitated due to the composition of the textile planar structure.

It is understood that with respect to use of silk, natural silk is preferably used, such as for example the mulberry silk or the tussah silk.

Furthermore, silk, respectively, the textile planar structure exhibits an especially good capacity for being cut based on the knit characteristics, which is particularly advantageous when used intraoperatively. Also, silk is easy to clean.

It is particularly advantageous, when the textile planar structure is provided with at least one base carrier which is saturated with protease inhibitor. For example, it is thus possible to apply the carriers with growth factors such as for example cytokines which facilitate the healing process. Preferably, the base carrier is provided in the form of a fiber.

It is understood that in particular the base carrier of the textile planar structure can also incorporate further inhibitors which may also contain antibiotic and antibacterial substances.

In order to promote the healing process in an advantageous manner, the textile planar structure can incorporate resorbant material. Such a material can under certain circumstances also react with the injured area. Advantageously, the resorbant material can influence the permeability in that for example, by means of the resorbant material, the size of the pores can be varied.

Depending on the use, it is advantageous when the textile planar structure is provided with a coating, so that the wound dressing can, for example be coated with hyaluronacid or collagen.

Furthermore, it is advantageous, when the textile planar structure has a surface which can be modified through application of heat or pressure.

Calendaring is for example one type of modification that can be applied and which can also be carried out under heat. Thereby, the textile planar structure is placed between two rollers of a press, with the surface of the rollers made from metal or elastic material, whereby the surface can be configured particularly smoothly.

The afore-described textile planar structure has favorable effect on the healing process in such a manner that oftentimes, beginning from the third day, an open wound treatment can be carried out. Depending on the circumstances, it is also possible to let the wound dressing remain until reepithelization has been completed. Thus, after the wound has healed, the wound dressing oftentimes peels away by itself.

Ideally, removal of the protective dressing is done at the latest 5 days after start of treatment.

It has been shown that after removal of the protective dressing and completed open wound healing no further bandage changes are necessary.

Those skilled in the arts understand that the textile planar structure can also be provided with seams by means of sewing and knitting processes. It is also possible to combine several textile planar structures, also as superposed structures by knitting or sewing methods, to thereby conform the wound dressing exactly to the size and extension of the injured site.

In particular with large injury sites, respectively large wounds, no overlap of wound dressings when using several is necessary on the one hand, nor is overlap with healthy tissue, respectively intact skin necessary.

It is understood that it is advantageous, when the wound dressing material can be provided as yardage, that the preferred width of the material is less than 4 m. With this dimension virtually every possible size and configuration of a wound bandage can be realized.

Preferably, the wound dressing is provided in prepackaged and sterilized form for various sizes of wounds and applications.

Those skilled in the art will also recognize that the textile planar structure is easily manufactured in precut and prepared shapes, such as for example, in the shape of a glove, aside from the production of a knitted glove.

Accordingly, it is an object of the invention with respect to a glove for dressing a wound, to provide a glove which is made from the afore-described textile planar structure. The glove is in particular suitable for the treatment of skin burns, since the glove envelopes the fingers and the surface of the hand especially well and thus efficiently protects the injured area. In comparison, with conventional wound dressings, the fingers of the hands especially and also the hands themselves remain mobile right from the start of treatment, to thus greatly reduce the danger of the frequently occurring stiffness and/or the danger of at least temporary loss of function or temporary loss of motion. In this manner, the glove differs substantially from the conventional wound dressings, in particular, since silk makes for addressing, which is not static and which advantageously allows movement by the patient and applying physical therapy exercises right after the start of treatment.

It is another aspect of the invention to provide a process for the production of a wound dressing from the textile planar structure as afore-described, wherein the textile planar structure is formed as a wound dressing intraoperatively. It is advantageous to know in advance what the configuration of the wound dressing should be, so that the wound dressing can be prepared beforehand and is ready for immediate use. However, the extent of injury may not be foreseeable, or respectively, during the treatment, unexpected changes have to be made with respect to the injured site, so that the surgeon is able to adjust the dressing by cutting suitable pieces of the dressing.

The planar structure can however also be formed by sewing it in such a manner so as to create a three-dimensional wound dressing. For example, this can be a glove or another type of wound dressing whereby a body part can also be completely wrapped.

BRIEF DESCRIPTION OF THE DRAWING

Other advantages, aspects and properties of the present invention are explained by means of the figure showing an example of a wound dressing.

FIG. 1 shows a top view of a wound dressing applied to an injured site.

DETAILED DESCRIPTION OF PREFERRED EMBODIMENTS

The wound dressing 1 is applied to an injured site 2. The injured site 2 is shown by means of a circumferential line 3, so that the wound dressing 1 in this embodiment is also disposed in area 4 around the injured area 2 and thereby the wound dressing generously overlaps the injured area 2.

The wound dressing 1 has thus two main directions of extensions 5 and 6, wherein the main direction of extension 5 extends in direction of a stitch row 5A of wound dressing 1 and the main direction of extension 6 extends orthogonal to the stitch row 5A of wound dressing 1. The main direction of extension 6 extends accordingly along the stitch wale 6A.

The wound dressing 1 is attached by means of clamps 7, 8, 9, 10 in the area 4 at the healthy skin tissue 12. For example, Delta clamps can be used as clamps.

Wound dressing 1 consists of silk fiber (not shown here) and produced as knitted material (not shown here). Due to its knitted character, the wound dressing exhibits a good firmness for cutting.

Thus, the wound dressing 1 is produced in such a manner, that the elasticity in the main direction of extension. 5 and 6 is nearly identical and the basis for its homogenous, respectively quasi-isotropic extension properties, at least along the main directions of extension 5 and 6.

The wound dressing 1 has a surface 11, which is modified through pretreatment by means of heat and pressure. Thus, for example, an especially smooth surface can be obtained, which later on can facilitate a spontaneous removal of the wound dressing 1 from the injured area 2. Furthermore, due to the smooth surface, micro traumata and pain caused thereby such as for example, after split skin removal, which occurs, among others, through contraction of muscle group under the removal area are thus avoided or at least reduced.

With respect to this embodiment, by means of the pretreatment with heat and pressure, the elasticity behavior was adjusted to physiological requirements.

The wound dressing 1 is placed onto the injured area 2 through a temporary dressing of compresses (not shown here) of tissues (not shown here) which are saturated with vasoconstrictive medication (e.g. Suprarenin).

The slight overlap shown in the embodiment of wound dressing 1, in the area 4 is not absolutely required, but provides a distinct advantage, especially when treating extreme burn injured patients having large burn areas 2 and if applicable, in areas of limited split skin removal. Subsequently, a protective dressing is applied (not shown here) with sterile dressing material. The protective dressing is removed after 3 to 5 days and an open wound treatment carried out.

The wound dressing 1 side facing away from the body, respectively the skin 12 dries up, while at the side facing the wound area a moist wound milieu develops, thereby providing optimal regeneration conditions to the skin. The wound dressing 1 is adhered to the injured site 2 and remains at the injured site 2 up until reepithelization is completed. In the further course of the treatment, the wound dressing 1 removed from the already healed area is removed for example by means of scissors.

The formation of a local wound infection is easily detected by the formation of fluid underneath the wound dressing 1 as well as the lack of adherence of the wound dressing at the injured site 2. In contrast to a wound coverage with "Biobrane", the wound dressing 1 can be remoistened with the hydrophilic solutions (e.g. PVP-Iodine, Lavasept, Chlorhexidin or mefenidacetate) in order to repair the infection.

The removal of the wound dressing 1 from injured site 2 is spontaneous. After removal of the protective dressing (not shown here) and open wound treatment, no further changes in dressing are necessary.

In particular due to the identical stretching properties of wound dressing 1 in the main directions of extensions 5 and 6, a posttraumatic restriction of movement is to a large extent prevented. This is particularly so when the injured site 2 on a hand, where due to the material properties of wound dressing 1, a glove can be provided for treating the injured site.

The wound dressing 1 comprises a fiber material 13 (shown here only by way of example) from a resorbant polymer, which is optionally saturated with growth factors. Thus, a wound healing can be optimized and accelerated through continuous release of cytokines.

While the invention has been disclosed in connection with the preferred embodiments shown and described in detail, various modifications and improvements thereon will become readily apparent to those skilled in the art, without departing in any way from the spirit of the present invention.

What is claimed as new and desired to be protected by Letters Patent is set forth in the appended claims:

1. A wound dressing suitable for being adhered to an injured skin comprising: no more than one layer, wherein the layer is a textile planar structure with a first main direction of extension and with at least one further main direction of extension, wherein the textile planar structure is a knit fabric constructed in a single layer and having a row of stitches and a row of stitch wales, said first main direction of extension extending along said row of stitches and said further main direction extending along said row of stitch wales, and wherein said knit fabric comprises more than 70% of silk and is free of elastomeric fibers, and wherein the extension properties of said first main direction of extension and said further main direction of extension vary from each other less than 80%, and wherein the knit fabric exhibits in the first and further main direction of extension a tissue stretching ε in the range of from 100% to 300%.

2. The wound dressing according to claim 1, wherein the textile planar structure exhibits at least in two of the main directions of extension substantially identical extension properties.

3. The wound dressing according to claim 1, wherein the planar structure has a thickness of less than 6 mm.

4. The wound dressing according to claim 3, wherein the thickness is more than 0.05 mm.

5. The wound dressing of claim 4, wherein the thickness is more than 0.1 mm.

6. The wound dressing of claim 3, wherein the thickness is less than 2 mm.

7. The wound dressing according to claim 1, wherein the planar structure has pores, said pores having a diameter of less than 2 mm.

8. The wound dressing according to claim 7, wherein the pores have a diameter of greater than 0.02 mm.

9. The wound dressing of claim 8, wherein the pores have a diameter of greater than 0.08 mm.

10. The wound dressing of claim 7, wherein the diameter of the pores is less than 0.3 mm.

11. The wound dressing according to claim 1, wherein the textile planar structure has at least a basic carrier comprising a protease inhibitor.

12. The wound dressing according to claim 1, wherein the textile planar structure comprises a resorbant material.

13. The wound dressing according to claim 1, wherein the textile planar structure has a coating.

14. The wound dressing (1) according to claim 1, wherein the textile planar structure has a surface which is modified through heat and pressure.

15. A glove for applying to an injured skin, comprising the textile planar structure according to claim 1.

16. A method for producing a wound dressing, comprising providing a textile planar structure according to claim 1, and forming the textile planar structure intra-operatively as a wound dressing.

17. A wound dressing suitable for being adhered to an injured skin comprising: a single layered textile planar structure with a first main direction of extension and with at least one further main direction of extension, wherein the single layered textile planar structure is a knit fabric constructed as a single layer and having a row of stitches and a row of stitch wales, said first main direction of extension extending along said row of stitches and said further main direction extending along said row of stitch wales, and wherein said knit fabric comprises more than 70% of silk and is free of elastomeric fibers, wherein the wound dressing adhered to a burn wound facilitates reepithelization after which the wound dressing spontaneously removes and wherein the extension properties of said first main direction of extension and said further main direction of extension vary from each other less than 80%, and wherein the knit fabric exhibits in the first and further main direction of extension a tissue stretching $\varepsilon$ in the range of from 100% to 300%.

* * * * *